United States Patent [19]
Prockop et al.

[11] Patent Number: 5,786,341
[45] Date of Patent: Jul. 28, 1998

[54] USE OF A COL1A1 MINI-GENE CONSTRUCT TO INHIBIT COLLAGEN SYNTHESIS

[75] Inventors: Darwin J. Prockop, Philadelphia, Pa.; Jaspal Khillan, Cherry Hill; Shi-Wu Li, Collingswood, both of N.J.; Ruth Pereira, Philadelphia, Pa.

[73] Assignee: Thomas Jefferson University, Philadelphia, Pa.

[21] Appl. No.: 488,346

[22] Filed: Jun. 7, 1995

Related U.S. Application Data

[63] Continuation of PCT/US94/03321, Mar. 28, 1994, which is a continuation of Ser. No. 37,885, Mar. 26, 1993, abandoned.

[51] Int. Cl.$^6$ .......................... A61K 48/00; C07H 21/04; C12N 15/12; C12N 15/85
[52] U.S. Cl. ..................... 514/44; 435/172.3; 435/320.1; 435/325; 536/23.5; 536/24.5
[58] Field of Search ........................... 435/69.1, 172.3, 435/320.1, 325; 514/44; 424/93.2, 93.21; 536/24.5, 23.5

[56] References Cited

U.S. PATENT DOCUMENTS 4,736,866  4/1988  Leder et al. .......................... 800/1.001

OTHER PUBLICATIONS

Ala–Kokko et al., "Hepatic Fibrosis in Rats Produced by Carbon Tetrachloride and Dimethylnitrosamine: Observations Suggesting Immunoassays of Serum for the 7S Fragment of Ype IV Collagen area More Sensitive Index of Liver Damage than Immunoassays for the $NH_2$–Terminal Propeptide of Type III Procollagen", *Hapatology* 16:167–172 (1992).

Ala–Kokko et al., "Single base mutation in the type II procollagen gene (COL2A1) as a cause of primary osteoarthritis associated with a mild chondrodysplasia", *Proc. Natl. Acad. Sci. USA* 87:6565–6568 (1990).

Bonadio et al., "Transgenic mouse model of the mild dominant form of osteogenesis imperfecta", *Proc. Natl. Acad. Sci. USA* 87:6565–6568 (1990).

Byers, "Brittle bones—fragile molecules: disorders of collagen gen structure and expression", *TIG* 6:293–300 (1990).

Chang et al., "Antisense Inhibition of ras p21 Expression that is Sensitive to a Point Mutation", *Biochemistry* 30:8283–8286 (1991).

Chiang et al., "Antisense Oligonucleotides Inhibit Intercellular Adhesion Molecule 1 Expression by Two Distinct Mechanisms", *J. Biol. Chem.* 266:18162–18171 (1991).

Chomcynski et al., "Single–Step Method of RNA Isolation by Acid Guanidinium Thiocyanate–Phenol–Chloroform Extraction", *Anat. Biochem.* 162:156–159 (1987).

Chu et al., *Connective Tissue and Its Heritable Disorders*, Chapter 3, Part II, pp. 249–265 (1993).

Khillan et al., "Transgenic Mice That Express a Mini–gene Version of the Human Gene for Type I Procollagen (COL1A1) Develop a Phenotype Resembling a Lethal Form of Osteogenesis Imperfecta", *J. Biol. Chem.* 266:23373–23379 (1991).

Kole et al., "Pre–mRNA splicing as a target for antisense oligonucleotides", *Adv. Drug Del. Rev.* 6:271–286 (1991).

Kuivaniemi et al., "Mutations in collagen genes: causes of rare and some common diseases in humans", *FASEB J.* 5:2052–2060 (1991).

Marmur et al., "Determination of the Base Composition of Deoxyribonucleic Acid from it Thermal Denaturation Temperature", *J. Mol. Biol.* 5:109–118 (1962).

Mooslehner et al., "Two mRNAs of mouse pro α1(I) collagen gene differ in the size of the 3'–untranslated region", *Nucleic Acids Research* 16:773 (1988).

Munroe, "Antisense RNA inhibits splicing of pre–mRNA in vitro", *EMBO J.* 7:2523–2532 (1988).

Myers et al., "Cloning a cDNA for the pro–α2 chain of human type I collagen", *Proc. Natl. Acad. Sci USA* 78:3516–3520 (1981).

Olsen et al., "High Levels of Expression of a Minigene Version of the human Proα1(I) Collagen Gene in Stably Transfected Mouse Fibroblasts", *J. Biol. Chem* 266:1117–1121 (1991).

Orkin, *The Molecular Basis of Blood Diseases*, G. Stamatoyannopoulous et al. Eds., W.B. Saunders, Philadelphia, pp. 106–126 (1987).

Prockop et al., *Ann N.Y. Acad. Sci.* vol. 580, (1990) pp. 330–339.

Prockop, "Minireview: Mutations That Alter the Primary Structure of Type I Collagen", *J. Biol. Chem.* 265:15349–15352 (1990).

Slack et al., "An Upstream Regulatory Region Mediates High–Level Tissue–Specific Expression of the Human α1(I) Collagen Gene in Transgenic Mice", *Molecular and Cellular Biology*, Apr. 1991, pp. 2066–2074.

Stacy et al., "Perinatal lethal osteogenesis imperfecta in transgenic mice bearing an engineered mutant pro–α1 (I) collagen gene, *Nature* 332:131–136 (1988).

Stein et al., "Oligodeoxynucleotides as Inhibitors of Gene Expression: A Review", *Cancer Research* 48:2659–2668 (1988).

Sykes, "Bone disease cracks genetics", *Nature* 348:18–20 (1990).

(List continued on next page.)

*Primary Examiner*—Douglas W. Robinson
*Assistant Examiner*—Amy J. Nelson
*Attorney, Agent, or Firm*—Pennie & Edmonds LLP

[57] ABSTRACT

Methods are provided for controlling the synthesis of protein from the human gene for the proα1(I) chain of type I procollagen in cells using mini-gene constructs which are injected into cells which synthesize the protein. Methods for controlling collagen deposition in tissue mini-gene constructs are also provided.

2 Claims, 6 Drawing Sheets

OTHER PUBLICATIONS

Vanderberg et al., "Expression of a partially deleted gene of human type II procollagen (COL2A1)", *Proc. Natl. Acad. Sci* 88:7640–7644 (1991).

Vu et al., "Internucleotide Phosphite Sulfurization with Tetraethylthiuram Disulfide, Phosphorothioate Oligonucleotide Synthesis Via Phophoramidite Chemistry", *Tetrahedron Letters* 32:3005–3008 (1991).

Vuorio et al., *J. Cell. Biochem.* Supp. 15A (Jan. 1991) p. 205, Abstract No. B423.

Westerhausen et al., "Completion of the Last Half of the Structure of the Human Gene for the Proα1(I) Chain of Type I Procollagen (COL1A1)", *Matrix* 11:375–379 (1991).

Williams et al., "Synthesis and Processing of a Type I Procollagen Containing Shortened Pro–α1(I) Chains by Fibroblasts form a Patent with Osteogenesis Imperfecta", *J. Biol. Chem.* 258:5915–5921 (1983).

Wu et al., "Human–Mouse Interspecies Collagen I Heterotrimer Is Functional During Embryonic Development of Mov13 Mutant Mouse Embryos", *Molecular and Cellular Biology* 10:1452–1460 (1990).

Uhlmann et al., "Antisense Oligonucleotides: a new therapeutic principle," *Chemical Reviews* 90(4):544–579 (1990).

Nussbaum et al., Abstract No. 1505, 42nd Annual Meeting, San Francisco, CA, *The American Society of Human Genetics*, Nov. 9–13, 1992.

Wickstrom, "Strategies for administering targeted therapeutic oligodeoxynucleotides", Tibtech 10:281–287 (1992).

Ledley et al., "Clinical considerations in the design of protocols for somatic gene therapy", *Human Gene Therapy* 2:77–83 (1991).

Prockop et al., *Ann. of the NY Acad. of Sci.* 580:330–339 (1990).

Stull RA, et al. "Antigene, ribozyme and aptamer nucleic acid drugs: Progress and prospects." Pharmaceutical Research 12 (4): 465–483., 1995.

Orkin SH, et al. "Report and Recommendations of the Panel to Assess the NIH Investment in Research on Gene Therapy.", Dec. 7, 1995.

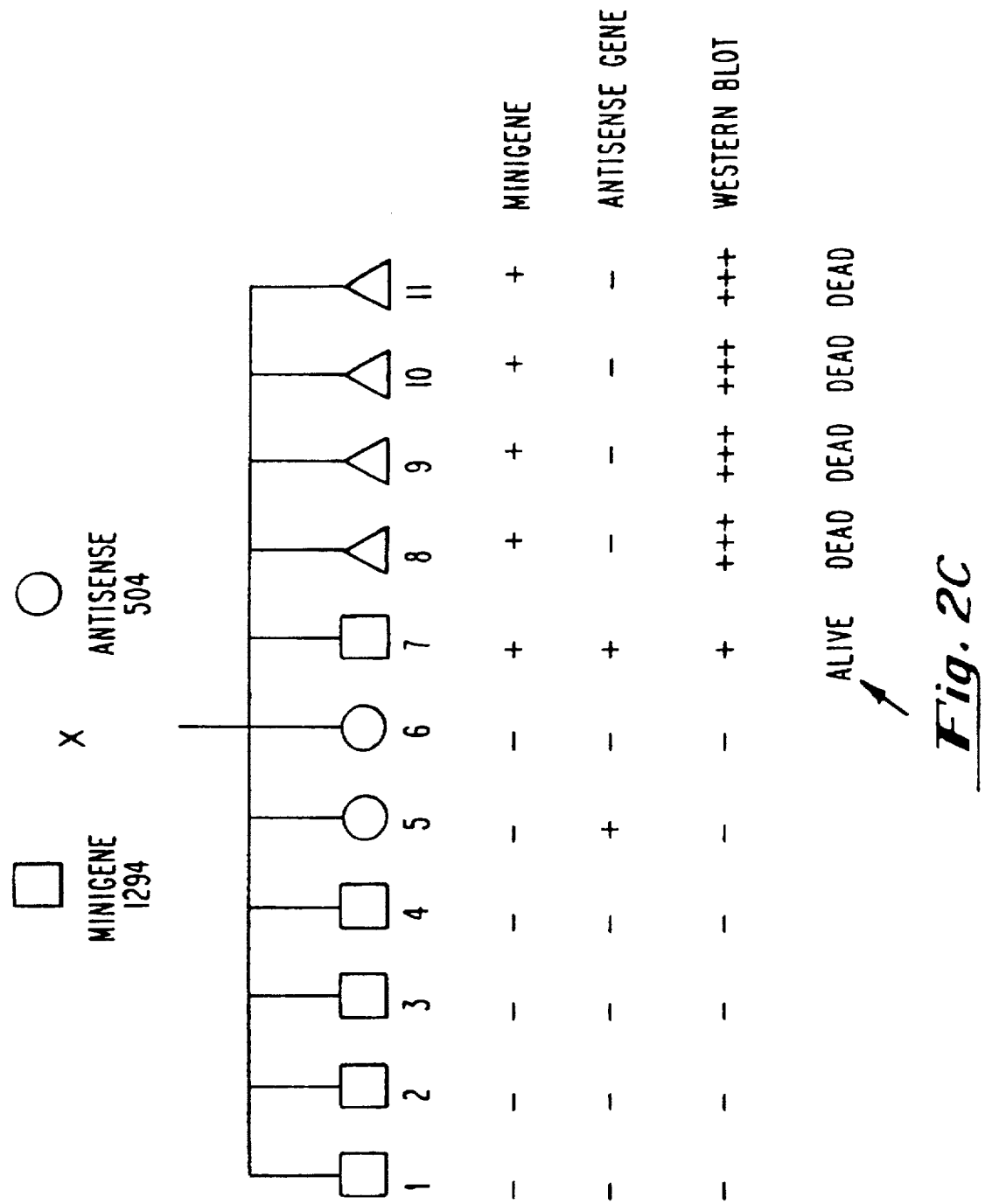

USE OF A COL1A1 MINI-GENE CONSTRUCT TO INHIBIT COLLAGEN SYNTHESIS

This is a continuation of international application Ser. No. PCT/US94/03321 filed on Mar. 28, 1994, which is a continuation of U.S. Ser. No. 08/037,885, filed Mar. 26, 1993, now abandoned.

BACKGROUND OF THE INVENTION

A number of inherited diseases have recently been shown to be caused by mutations in collagen genes that either cause synthesis of insufficient amounts of collagen or defective collagen, but other human diseases are caused by overproduction of normal collagen in a form referred to as either fibrotic tissue or scars. Deposition of collagen is a normal part of the repair process that occurs when any tissue is injured. In man, however, the collagen deposition that occurs is frequently excessive and irreversible. The result is replacement of normal cells and tissues with inert collagen in the form of tough fibers. There are many examples of this excessive deposition of collagen. One example is injury to the skin following trauma, burns or surgery. In normal people, scars form because some of the cells in the skin (fibroblasts) synthesize excessive amounts of collagen that are deposited as scar tissue before the cells that synthesize the outer layers of the skin (epithelial cells) can regenerate themselves and form normal skin over the area of injury. In some individuals, particularly Asians and Blacks, the deposition of collagen is extreme so that large tumors consisting almost entirely of collagen fibers called keloids and form at the site of even a minor injury such as a small surgical incision and become a source of serious disfigurement and discomfort. Excessive deposition of collagen as scars of the skin is a major problem in some types of animal husbandry. Most horses, for example, form large collagen deposits called "proud flesh" with almost every injury below the knee and many have to destroyed as a result. Excessive deposition of collagen in man also occurs after injury or surgery of internal organs. For example, excessive fibrosis or scarring frequently occurs following injury or surgery of the hand and is a significant cause of permanent work disability among mechanics. Surgery to the back for herniated disks and related problems frequently fails to improve the status of the patient because excessive deposits of collagen form around the sites of surgical repair and produce pain and dysfunction because they impinge on nerves. Excessive deposit of collagen fibers is also a major feature of cirrhosis of the liver. When the liver is damaged by viruses, alcohol or toxic materials, a competition occurs between the replication of normal liver calls (hepatocytes) and collagen-producing cells that deposit collagen fibers. The deposition of collagen usually wins out in this competition and, as a result, the liver becomes non-functional and cirrhotic ("hard") because the normal tissue is largely replaced by collagen fibers. A similar sequence of events is frequently seen in the lung where injury from a number of agents, including many agents used in cancer chemotherapy, is followed by replacement of normal lung tissue so that the lung becomes stiff and can no longer exchange oxygen and other gases. The resulting condition (pulmonary interstitial fibrosis) is frequently lethal. A similar type of pulmonary fibrosis also occurs in some individuals for unknown reasons. In addition, excessive deposition of collagen fibers can be a general phenomenon of some diseases. In the condition known as progressive systemic sclerosis, excessive amounts of collagen are deposited in the skin and many other organs. The patients are described as becoming "encased in leather".

The result can be a total inability to use the hands, to open the mouth to eat, or to absorb nutrients from the gastrointestinal tract. Many of the patients die because internal organs such as the kidney are replaced by collagens.

Excessive deposition of collagen has also been implicated, but not demonstrated as directly, as a major debilitating event in atherosclerosis and arteriosclerosis where the "hardening" of the blood vessels is explained in part by the fact that they contain more collagen. Excessive deposition of collagen has also been implicated as a secondary explanation for the muscle failure in muscular dystrophy. Also, it has been implicated in some blood diseases in which the blood-producing cells of bone marrow are replaced by collagen fibers (myelofibrosis).

Overall, therefore, there are important needs for developing means of limiting and controlling the deposition of normal collagen in tissues. No effective measures are currently available.

SUMMARY OF THE INVENTION

A method for controlling the synthesis of protein from the human gene for the pro$\alpha$1(I) chain of type I procollagen in cells is provided comprising a gene selected from the group consisting of a mini-gene construct of the human gene for the pro$\alpha$1(I) chain of type I procollagen and a mini-gene construct of the human gene for the pro$\alpha$1(I) chain of type I procollagen with the second half of the gene sequence being antisense; placing one or both genes in a modified virus selected from the group consisting of a retrovirus and an adenovirus; and infecting cells capable of synthesizing protein from the human gene for the pro$\alpha$1(I) chain of type I procollagen with the modified virus containing the mini-gene construct or constructs.

The mini-gene contains an internal deletion of the COL1A1 gene whereby 42 exons (exons 4 to 46) and most of the associated introns have been removed.

A method for controlling collagen deposition in tissue is also provided comprising providing a gene selected from the group consisting of a mini-gene construct of the human gene for the pro$\alpha$1(I) chain of type I procollagen and a mini-gene construct of the human gene for the pro$\alpha$1(I) chain of type I procollagen with the second half of the gene sequence being antisense; combining one or both mini-gene constructs with a selected delivery means; and delivering one or both mini-gene constructs to the tissue wherein the collagen deposition is to be controlled. In one embodiment, the delivery means comprises a composition containing a protein or lipid or other molecules chemically linked to one or both mini-gene constructs. In other embodiments, the delivery means comprises an electrical current, laser beam, or pressure. The mini-gene construct or constructs may be administered by injection, direct topical application, inhalation, or orally.

In another embodiment of the invention, a method of treating a mammal having a condition characterized by the excessive deposition of collagen in tissue comprising administering a therapeutically effective amount of a composition consisting essentially of a gene selected from the group consisting of a mini-gene construct of the human gene for the pro$\alpha$1(I) chain of type I procollagen and a mini-gene construct of the human gene for the pro$\alpha$1(I) chain of type I procollagen with the second half of the gene sequence being antisense and a pharmaceutically acceptable carrier to a mammal having a condition characterized by the excessive deposition of collagen in its tissue. The condition characterized by the excessive deposition of collagen in tissue may

3 be a cirrhotic or fibrotic disease. Cirrhosis of the liver, pulmonary interstitial fibrosis, progressive systemic sclerosis, atherosclerosis, arteriosclerosis, and myelofibrosis may be treated with the methods of the invention. The invention may also be used to treat conditions resulting from injury to the skin of the mammal following trauma, burns, surgery or the result of injury or surgery of internal organs.

Composition of the invention may be administered by injection, direct application, inhalation, or orally.

DESCRIPTION OF THE DRAWINGS

FIG. 1(A) shows the structure of the mini-gene for the proα1(I) chain of human type I procollagen. The gene contains 2,300 bp of the promoter region, about 2,000 bp of 3'-sequences sequences, and all of the gene except for exons 6 to 46 and most of the associated introns. Because the deletion of coding sequences was in-frame, the deleted gene codes for a shortened proα1(I) chain. FIG. 1B shows the structure of the antisense mini-gene construct. The 3'-half of the mini-gene (A) has been inverted so that the second half of the gene has a base sequence that is complementary to the sequences for exons 47 to 52 and the associated introns of the human gene of proα1(I) chains of type I procollagen.

FIGS. 2A–2D show typical pedigrees from experiments in which a line of transgenic mice expressing high levels of the mini-gene was bred with a line expressing the antisense gene. As indicated, all mice inheriting the mini-gene only were dead at birth. All mice inheriting the antisense gene only were viable and had no phenotype. All mice inheriting both genes were also viable and without a phenotype.

DETAILED DESCRIPTION OF THE INVENTION

The present invention offers methods for controlling collagen deposition in tissues. Mini-gene constructs useful in the methods of the invention are shown in FIG. 1. The mini-gene construct (FIG. 1) contains the first five exons and the last six exons of the gene together with 2.3 kb of the 5'-flanking sequence and about 2 kb of the 3'-flanking sequence. The 5' and 3' fragments of the gene are joined through an artificial SalI site located within two intervening sequences so as not to alter any sequences required for RNA splicing. Also, all the coding sequences were in frame. The structure of the construct was verified by mapping with restriction endonucleases and partial DNA sequencing. The 5'-end of the gene has an artificial NotI site. Thus, the construct can be excised cleanly from the plasmid vector with a NotI/BamHI restriction enzyme digestion.

Figure 1A:
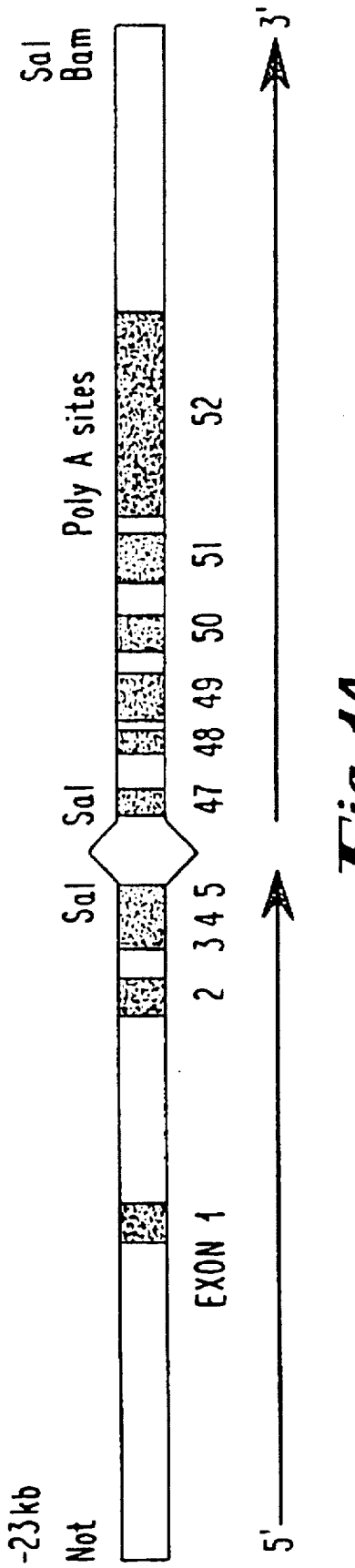
FIGS. 1A–1B show the structure of the mini-gene construct.

FIG. 1A shows a mini-gene construct of the human gene for the proα1(I) chain of type I procollagen (COL1A1). The gene is denoted a "mini-gene" because it contains an internal deletion whereby 42 exons (exons numbers 6 to 46) and most of the associated introns have been removed from the gene. This mini-gene has been used to produce transgenic mice that can be used for testing therapies for the treatment of osteogenesis imperfecta and osteoporosis, as described in Applicants' copending application Ser. No. 713,945. It was designed to cause synthesis of shortened proα1(I) chains of type I procollagen that bind to normal chains of the same protein and cause the degradation of the normal chains because a molecule containing both shortened proα1(I) chains, and normal proα1(I) chains cannot fold into a biologically functional molecule. As shown by Example 1 herein, expression of the mini-gene in transgenic mice produces a net decrease in the amount of type I collagen found in tissues such as bone that are normally rich in the protein. In the present invention, the same mini-gene is used to prevent excessive deposition of collagen by placing it in a modified virus or other composition that will serve to carry the mini-gene to cells producing excessive amounts of collagen and cause synthesis of shortened proα1(I) chains in the cells. As a result, the amount of collagen synthesized and deposited as collagen fibers by the cells decreases.

Figure 1B:
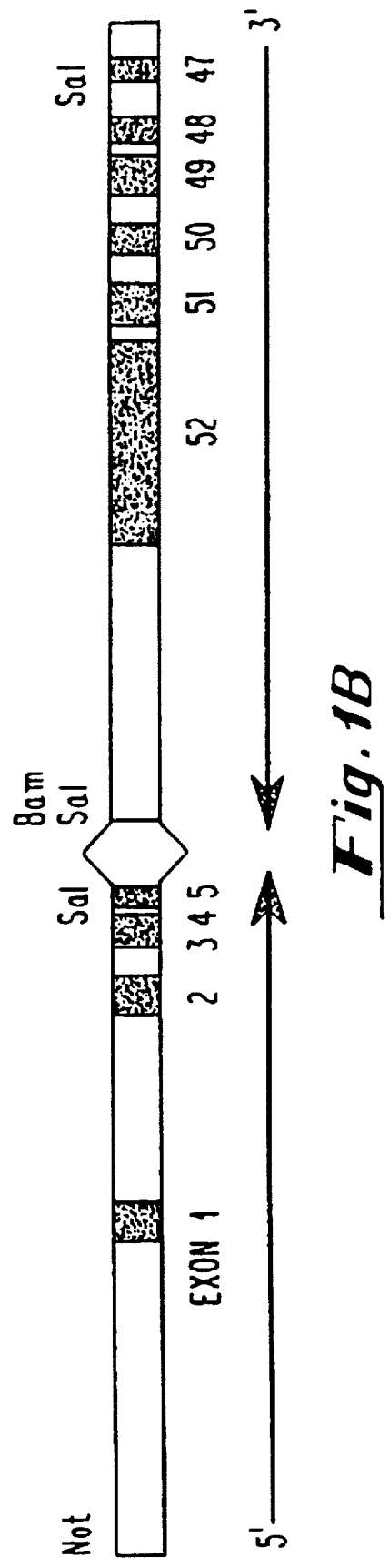
Figure 2A:
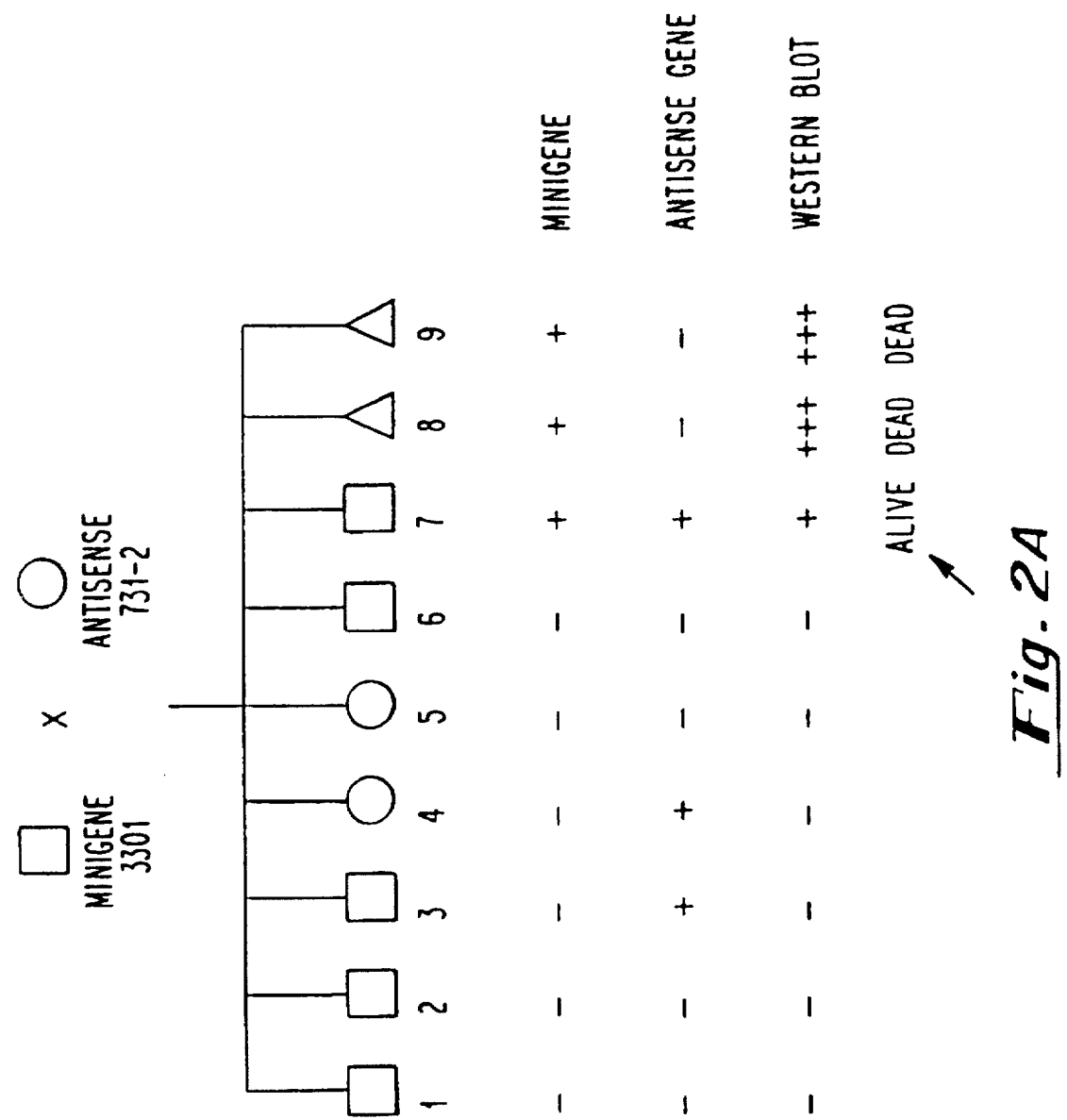
Figure 2B:
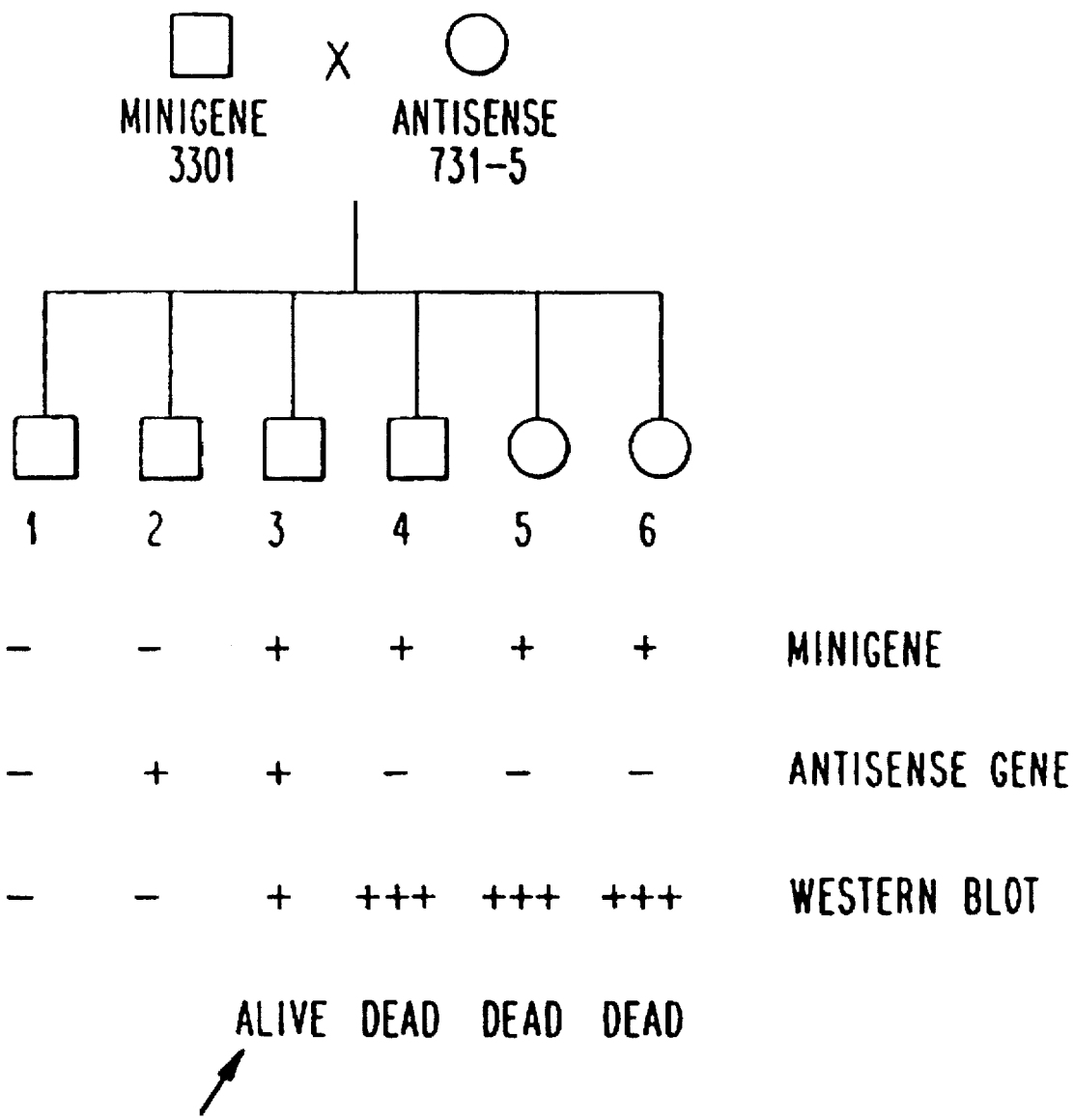
Figure 2D:
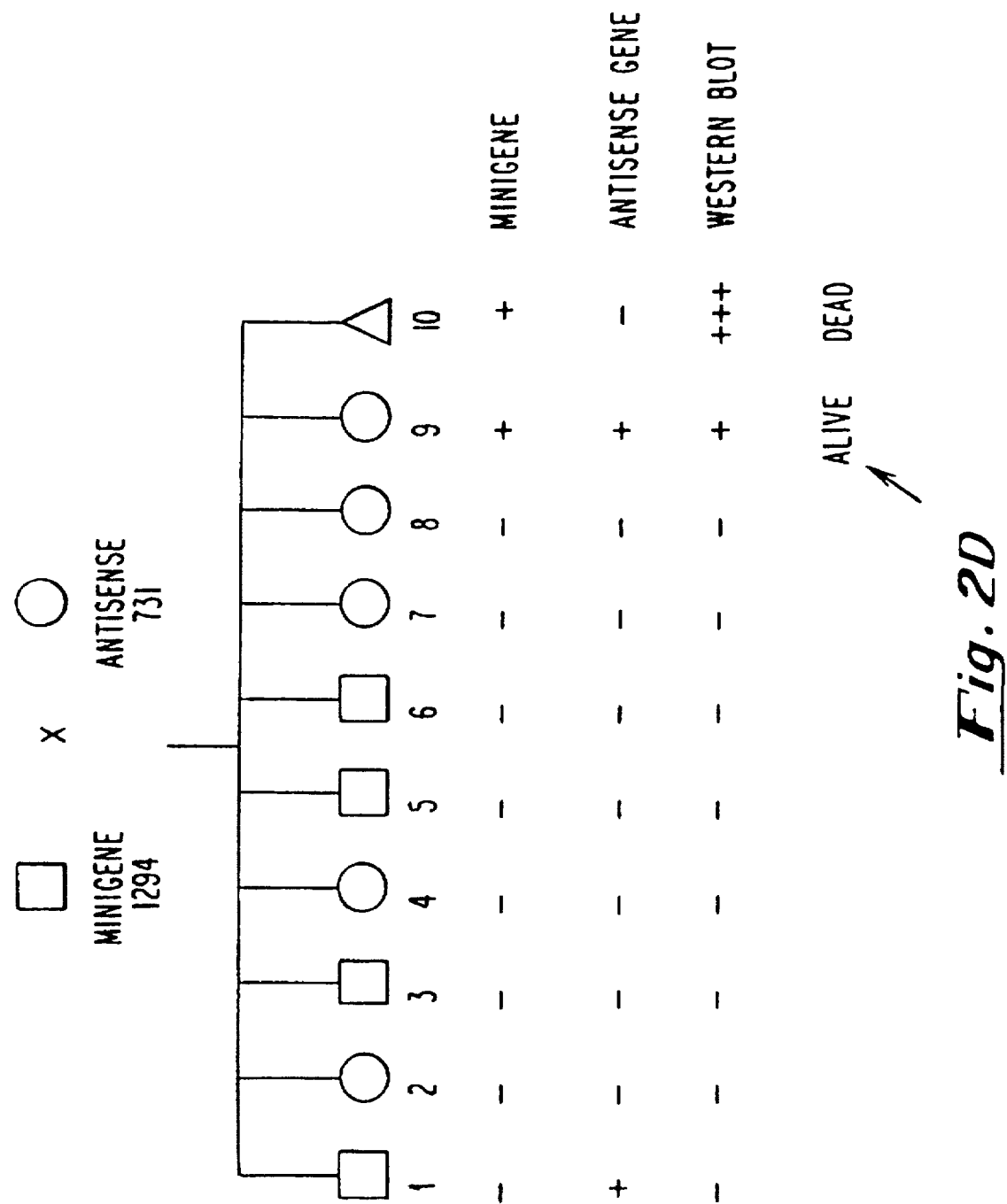

Another embodiment is illustrated in FIG. 1B. Here, the second half of the mini-gene is inverted so that the second half codes for complementary or antisense sequences of RNA bases for exons 47 to 52 and the associated introns. Because the second half of the "antisense gene" codes for a complementary sequence, the RNA transcribed from the gene will bind to the RNA transcribed from a normal gene for proα1(I) chains of the same cell. Because part of the normal RNA is rendered double stranded, it cannot be used to synthesize protein. Instead, it either becomes trapped in the nucleus of the cell or is degraded, probably by an enzyme that specifically degrades double-stranded RNA such as ribonuclease H. As shown by Example 2, expression of the antisense gene in transgenic mice can inhibit expression of a human gene for the same protein in a highly specific manner. Therefore, the method for inhibiting excessive deposit of collagen is to place the antisense gene in a modified virus or other composition that will serve to carry the antisense gene to cells producing excessive amounts of collagen and cause synthesis of an antisense RNA in the cells and, therefore, reduce the amount of collagen synthesized and deposited as collagen fibers by the cells.

Similar means can be used to deliver for the mini-gene and antisense gene to cells. For example, either one or both of the genes can be placed in modified RNA virus (retrovirus) that is engineered so that the virus will infect cells but will not generate any replicative virus that can infect a second generation of cells. Specific examples of the design and use of such retroviruses for the delivery of genes to cells are described in Tolstoshev, P., *Bone Marrow Transplantation* 1992, 9, 148–150 and Morgen, R. A. et al., *Nucleic Acids Research* 1992, 20, 1293–1299. As another example, either one or both of the genes can be placed in an appropriately modified virus that in its native form causes respiratory diseases (adenovirus) and the modified virus containing either gene can be used to infect cells producing excessive amounts of collagen. Examples of the use of such adenoviruses to deliver genes to cells are described in Engelhardt and Wilson, J. Pharmacy and *Pharmacology* 1992, 44, 165–167; Yoshimura et al., *Nucleic Acids Research* 1992, 20, 3233–3240 and Crystal, R. *Am J of Medicine* 1992, 92, 445–555.

The mini-gene and the antisense gene constructs are specifically designed to control the synthesis of protein from the human gene for the proα1(I) chain of type I procollagen. Controlling the synthesis of protein from this gene is appropriate because the vast majority of the collagen found in scars and fibrotic tissues is type I collagen which cannot be synthesized by cells without proα1(I) chains of the precursor molecule known as type I procollagen. The present invention, however, also includes other versions of mini-gene constructs in which other regions are deleted or specific base sequences are replaced. In particular, it may be useful to replace the promoter region (from exon 1 to –2.3 kb) with other promoters or combinations of promoters and enhancers from other genes that will improve transport to, or the controlled expression of, the gene in specific cells. Similar variations of the design of the antisense gene are also contemplated. Also, in addition to viruses as vectors for delivery of the genes, the present invention also contemplates other means of delivery such as incorporation of one or both genes into compositions that will facilitate entry of the genes and facilitate control of their expression in cells. For example, it may be useful to chemically link one or both kinds of genes to proteins, lipids or other molecules that will facilitate binding of the genes to specific cells and entry into their nuclei. Also, it may be useful to encapsulate one or both kinds of genes in lipids or viral capsules or similar molecules for the same purpose. The present invention also includes delivery of one or both kinds of genes to cells by means assisted by physical techniques such as electrical currents, ionic beams, laser beams or pressure. In using both kinds of genes to control fibrosis, it is contemplated that they can be used both for systemic administration to man and other animals and for local administration. For example, one or both kinds of genes in an appropriate composition can be administered by injection either into a vein, a muscle or under the skin. In an appropriate composition such as a virus vector, they can be administered by mouth. Also, they can be administered by direct application to the site of an injury or surgical incision in tissues such as the skin, the hand, or the back, to limit the amount and extent of the fibrosis and scarring that will occur. In addition, they can be administered to the lungs by inhalation as aerosols. For direct application to tissues, the genes can be in compositions that are in solution, in particulate suspensions, in oily compounds, in gels, or in solid materials that either remain in the tissues for extended periods of time or are rapidly absorbed or degraded by the tissues.

The invention is further illustrated by the following, non-limiting examples.

EXAMPLES

Example 1

A series of experiments were carried out to demonstrate that the mini-gene for human proα1(I) chains (FIG. 1A) can be used to specifically control the amount of type I collagen fibers deposited in tissues.

Lines of transgenic mice expressing the mini-gene were prepared by injecting fertilized eggs from matings of inbred FVB/N males and females, and the eggs were transferred either on the same day or cultured to the two cell stage and then transferred to the oviduct of a 0.5 day post-coitus pseudo-pregnant female. To identify progeny that contained the transgene in their genomes, DNA in a sample of tail or other tissue was analyzed for presence of the mini-gene as described in Examples 3 and 4.

To determine the effect of expression of the mini-gene on the collagen content of tissues, a line of transgenic mice was selected that expressed moderate levels of the transgene as both mRNA and protein. The line was propagated by brooding to wild-type mice from the same FVB/N inbred strain. As indicated in Table I, about 6% of the mice died at birth or shortly thereafter. About one-third developed spontaneous fractures but were viable. The remaining transgenic mice had no evidence of fractures detectable by x-ray examination.

TABLE I

SUMMARY OF MOUSE PHENOTYPES AT BIRTH

| | Mice | | Phenotype of transgenic mice[a] | | |
|---|---|---|---|---|---|
| | Total | Trans genic | Lethal with fractures | Non-lethal with fractures | No fractures |
| idCOL1 × Wt[b] | 195 | 89 | 6% | 33%[c] | 61%[c] |
| idCOL1 × idCOL1 | 70 | 48 | 40% | ND[d] | ND[d] |

[a]Fractures detected by x-ray
[b]Matings of transgenic males (idCOL1) with wild-type (wt) females from the same line of mice (FVB/N).
[c]Values based on x-ray examination on day of birth of 15 viable transgenic mice from 5 litters.
[d]Not determined.

To assay the collagen content of tissues from the mice, the femurs were selected as tissues that can be clearly dissected from the animals in a manner that is largely free of other tissues and the total collagen content of the tissue readily compared among groups of animals. As indicated In Table II, the collagen content of the femurs in the transgenic mice was significantly less than the collagen content of femurs from control littermates that did not have the mini-gene in their genomes. The results directly demonstrated that the mini-gene can be used to limit the amount of normal collagen deposited in tissues in mammals.

TABLE II

COMPOSITION OF FEMURS FROM 6-WEEK OLD MALE MICE[a]

| | Length (mm) | Wet weight (mg) | Mineral (mg) | Collagen (mg) |
|---|---|---|---|---|
| Controls (n = 22) | 14.1 ± 0.39 | 58.46 ± 7.39 | 19.9 ± 1.87 | 4.3 ± 1.16 |
| Transgenics (n = 16) | 12.4 ± 1.38** | 42.4 ± 2.12** | 13.6 ± 5.39** | 2.9 ± 1.24** |

[a]Values are means ± standard deviation.
**$p < 0.001$ by the Student t-test.

Example 2

An experiment was carried out to demonstrate that the antisense gene (FIG. 1B) can be used to limit and control the synthesis of proα1(I) chains of type I procollagen. The design of the experiment was based on the availability of two different lines of transgenic mice, one line expressing high levels of a human mini-gene for the proα1(I) chains of type I procollagen (FIG. 1A) and the other line expressing an antisense version of the same gene (FIG. 1B). The line expressing high levels of the human mini-gene developed a lethal phenotype in that about 90% of the mice died at birth, because the mini-gene caused synthesis of shortened proα1 (I) chains that caused degradation of the normal proα1(I) and proα2(I) chains synthesized from the endogenous mouse genes. As a result, there was a marked decrease in the amount of type I collagen present in their tissues and their bones and other collagen-rich tissues were extremely fragile. In contrast, the transgenic mice expressing the antisense version of the same gene (FIG. 1B) were viable and showed no phenotype such as increased fragility of bones and other tissues. The lack of a phenotype in the transgenic mice was explained by the fact that the antisense gene, like the mini-gene, was a human gene and the human and mouse genes have a number of differences in their base sequences. Because of the differences, the RNA from the antisense gene does not significantly bind to the RNA from the mouse gene for proα1(I) chains and, therefore, does not reduce synthesis of type I collagen from the endogenous mouse genes. The experiment here consisted of breeding the small number of viable transgenic mice expressing high levels of the human mini-gene with transgenic mice expressing the antisense version of the same human gene. The question addressed in the experiment was whether mice that inherit both genes show decreased synthesis of shortened proα1(I) chains from the human mini-gene.

Transgenic mice from the two lines were bred and the progeny analyzed both for the presence of the two genes in their genomes and the synthesis of proα1(I) chains in their tissues. The presence of the genes was detected by Southern blot analysis of DNA from tail or other tissues with $^{32}$P-labeled DNA probes for specific fragments of the genes. The synthesis of proα1(I) chains was assayed by the steady-state intracellular levels of the chains as detected by Western blotting of protein extracts from tissues with polyclonal antibodies from rabbits that reacted with the COOH-terminal propeptides of proα1(I) chains from both the mouse gene and the human mini-gene.

A total of ten litters and 77 mice were obtained. Thirty-one of the mice had a normal genotype, 22 inherited the antisense gene only, 13 inherited the mini-gene only, and 11 inherited both genes. Twelve of the 13 mice inheriting the mini-gene only had the lethal phenotype. In contrast, only 3 of 11 of mice with both genes had a lethal, phenotype.

Figure 3A:
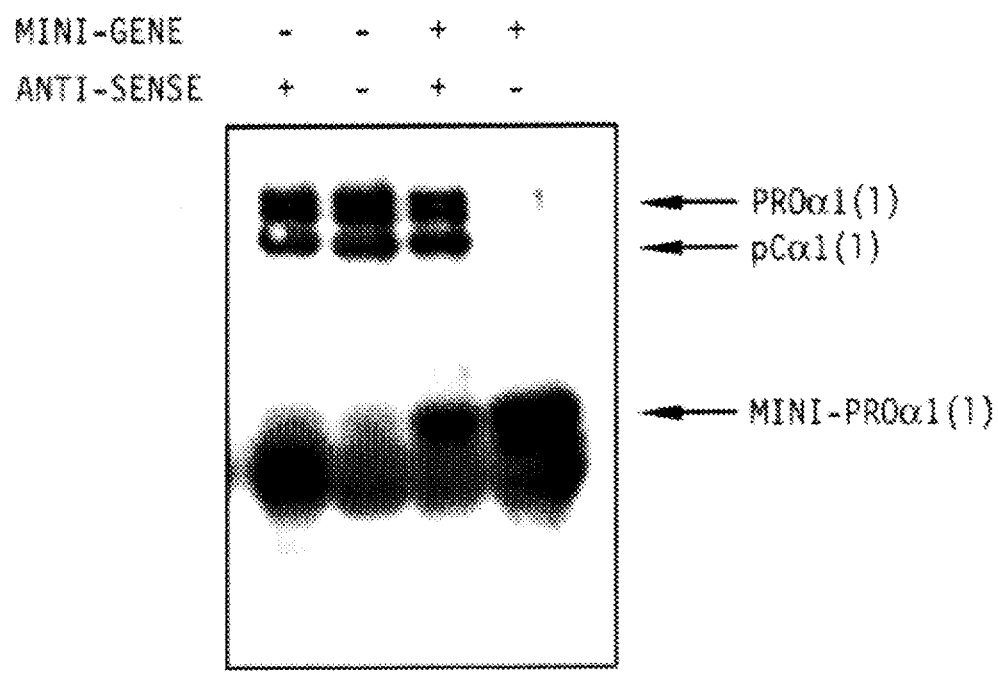
FIGS. 3A–3B show the results of western blotting experiments to demonstrate the effect of the antisense gene or expression of the mini-gene. Protein was extracted from samples of tail from mice breeding experiments such as those shown in FIG. 2. The proteins were separated by polyacrylamide gel electrophoresis in sodium dodecyl sulfate, the proteins were electroeluted onto filters, and the proteins were immunoblotted with a polyclonal antibody (rabbit) that reacts with the COOH-terminal propeptide in the proα1(I) chains of both mouse and human type I procollagen. Upper panel (3A): Immunoblot from selected members of one litter. The bands (top to bottom) in the immunoblot are proα1(I) chains of mouse type I procollagen; partially processed bands of mouse prα1(I) chains that retain the COOH-terminal propeptide; shortened proα1 (I) chains of human type I procollagen [mini-proα1(I)]; and a non-specific band of protein detected by the antibody. The results show that in the mouse inheriting both genes, there was a decrease In the steady-state level of intracellular shortened human proα1(I) chains [mini-proα1(I)] and an increase in mouse proα1(I) and pCa1(I) chains. Lower panel (3B): Similar results from a second litter.
Figure 3B:
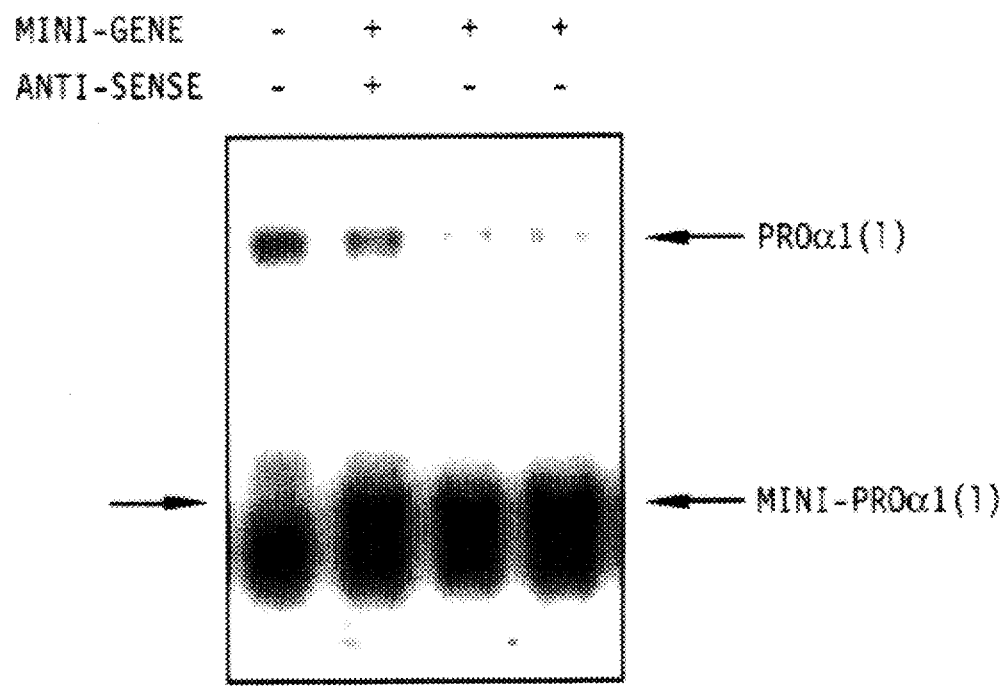

As indicated by the typical pedigree(s) in FIG. 2A–D, most of the mice that inherited only the mini-gene died at birth. In contrast, most of the mice that inherited both genes survived. As indicated by the examples in FIG. 3, there was a marked decrease in the synthesis of shortened human proα1(I) chains in tissues from mice that inherited both genes. Moreover, there was an increase in the normal proα1(I) chains synthesized from the endogenous mouse gene. Therefore, the results demonstrated that expression of the human antisense gene decreased synthesis of shortened proα1(I) chains from the human mini-gene in a highly specific manner.

X-ray examination of the mice revealed that all the mice with the mini-gene and the lethal phenotype had extensive fractures of long bones and ribs. Of the 11 mice with both genes, the two that died on the day of birth also had extensive fractures of long bones and ribs. The fractures in a third mouse that died on day 2 could not be evaluated because of maternal cannibalism. Therefore, the value of three out of 11 or 27% for a lethal phenotype in mice with both genes may be a slight overestimate. Three of the 11 mice with both genes had fractures of ribs that healed with callus formation when examined at one week. The remaining five of the 11 mice with both genes had no evidence of fractures.

To assay the effects of the antisense gene on expression of the mini-gene, extracts of tail from the mice were assayed by Western blotting with an antibody that cross-reacted with the full-length proα1(I) chains synthesized from the human mini-gene. In 11 mice that inherited the mini-gene only and developed the lethal phenotype, there was an apparent decrease in the mouse proα1(I) chains as indicated by a comparison of lanes in which about the same amounts of protein were loaded. More quantitative estimates were obtained by comparison of the ratio of mouse proα1(I) chains to mini-proα1(I) chains within the same sample and under conditions in which assays of the ratio are linear. The ratio was 0.64±0.128 S.D. (n=11) in mice within the mini-gene and the lethal phenotype. In contrast, the ratio was 1.23±0.686 S.D. (n=6) in mice with both genes and the normal phenotype. The difference in the mean was significant with a p value of 0.019 as estimated by the cumulative distribution of the standard normal distribution and a one-tail test. Tissue samples adequate for assay were available on only one of the three mice that inherited both genes and that had the lethal phenotype. In this one mouse, the ratio of normal to mini-proα1(I) chains was in the lower range of the values for transgenic mice that inherited the mini-gene only and had a lethal phenotype with extensive fractures.

As indicated in Table III, the effect of the human antisense gene was consistently observed in a series of breeding experiments in that there was a consistent decrease in the ratio of shortened proα1(I) chains to normal proα1(I) chains in mice that inherited both genes. Also, as expected, there was a consistent decrease in the lethal phenotype.

TABLE III

Effect of Antisense Gene on Lethal Phenotype

| | | Genotypes | | | |
|---|---|---|---|---|---|
| | | | Anti- | Both | |
| | | Mini- | sense | trans- | Phenotype (%) |
| Matings | Normal | Gene | gene | genes | Normal Lethal |
| Mini-gene | 44 | | | | 100 |
| × wild type | | 30 | | | 13   87 |
| Mini-gene | 31 | | | | 100 |
| × antisense | | | 22 | | 100 |
| gene | | 13 | | | 8   92 |
| | | | | 11 | 73   27* |

*Two mice died in a few hours and had extensive fractures of ribs and long bones. A third mouse died on the second day. It was smaller than littermates but because of maternal cannibalism, the phenotype of bony fractures could not be evaluated fully. However, it is listed here as a lethal phenotype.

TABLE IV

Phenotype of Transgenic Mice with Both the Mini-Gene and the Antisense Gene.

| | | | Ratio normal | Phenotype[b] | |
|---|---|---|---|---|---|
| Number | Genotype | | proα1 to | Lethal w/ | Viable |
| of mice | Mini- | Antisense | mini- | extensive | with |
| Normal | gene | gene | proα1[a] | fractures | fractures |
| 10 | + | | 0.64 ± 0.128 | 10 | |
| 7 | + | + | 1.23 ± 0.686 | 1[c] | 3   3 |

[a]Assayed by laser densitometry of Western blots similar to those shown in FIG. 5.
[b]Fractures in viable mice were assessed by x-ray analysis within the first week of life.
[c]Ratio of normal proα1(1) to mini-proα1(1) chains in mouse with the lethal phenotype was <0.39.

Overall, the results demonstrate that the human antisense gene can be used as a highly specific means of limiting and controlling synthesis by cells of the proα1(I) chain of type I procollagen that is essential to form the type I collagen and that is the major constituent of fibrous tissues and scars. Of special importance here is the observation that expression of the antisense gene did not significantly decrease synthesis of normal proα1(I) chains from the mouse gene. This result suggests that this action of the antisense gene is highly specific and that its expression is unlikely to have much effect on the expression of most normal genes whose base sequences are far more different from those of the human proα1(I) chains.

Example 3

Assays of Expression in Transfected Cells and Transgenic Mice

Assays of DNA and RNA

To assay for the presence of exogenous genes, standard Southern blotting is used (Maniatis et al., *Molecular Cloning, A Laboratory Manual* 1982). Restriction enzymes that give different size fragments from the exogenous and endogenous gene are identified. A sample of tail or other tissue was minced in 0.1M NaCl, 0.1M EDTA and 1% SDS in 50 mM Tris-HCl buffer (pH 7.5) containing 0.7 mg/ml proteinase K and incubated with agitation at 55° C. for 8 h to 15 h. The digested sample was extracted with phenol, phenol/chloroform/isoamyl alcohol and then with chloroform/isoamyl alcohol (24:1). The DNA was ethanol precipitated and dissolved in 10 mM Tris-HCl buffer (pH 7.5) and 1 mM EDTA. The isolated DNA was digested either with EcoRl, Kpnl/Clal, or HindIII. The digested samples were electrophoresed on 0.8% agarose gel and transferred onto a nitrocellulose filter. Filters were proved with the $^{32}$P-labeled mini-gene. Copy number of the type I mini-gene in transgenic mice was assayed by simultaneously proving the filters of HindIII digested DNA with the mini-gene or a cDNA (Hf677) for the human proα1(I) chain. The two DNA probes were mixed in equal amounts before labeling by nick translation with $^{32}$P to ensure about the same specific activity. X-ray films of the Southern blots were scanned on a densitometer to estimate the ratio of the exogenous and endogenous genes. For assay of gene copy number for the human proα1(II) mini-gene the filters were probed simultaneously with a 10 kb EcoRl-EcoRl fragment from the human gene and a 15 kb EcoRl-EcoRl fragment of the mouse gene for type II procollagen.

To assay expression of mini-genes as mRNA, standard Northern blot procedures are used. For RNA assays, total cellular RNA was isolated from tissues using the standard guanidine thiocyanate/cesium chloride procedure. Samples containing 3 to 10 µg of RNA were electrophoresed on 1% agarose formaldehyde gels and transferred to nitrocellulose filters. To detect expression of human exogenous genes as mRNAs, probe-protection experiments or a single probe that has only selective regions of identity with mouse or human mRNAs are employed. For example, the filters were hybridized with 1.5 kb insert from Hf677, a cloned cDNA for the human proα1(I) chain. Alternatively, an EcoRl/PvuII fragment of 563 nucleotides from the 5'-end of a human cDNA for the proα1(I) chain has been used in S1-nuclease probe-protection assays. The probe is fully protected by human mRNA for type I procollagen, but generates a distinctive fragment of 153 nucleotides with mouse mRNA. The probe is prepared as a single-stranded anti-sense RNA by subcloning into M13. The probe is labeled by using universal primer, the product is cleaved with restriction endonuclease, and the single-stranded probe isolated by polyacrylamide gel electrophoresis.

Assay of Protein Expression

Assays for expression of the genes at the protein level may also be performed. DNA transfected fibroblasts are taken directly for these assays. For transgenic mice, tissues were assayed directly or cultured fibroblasts or chondrocytes were prepared. For assay in mouse tissues about 50 mg of tissue was homogenized in 0.5 ml of 4M guanidine thiocyanate, 0.25M EDTA, 10 mM N-ethylmaleimide and 1 mM p-aminobenzamidine. For examination of reduced proteins, the homogenizing buffer also contained 10 mM 2-mercaptoethanol, a dithiothreitol (DDT). For examination of unreduced proteins, the buffer contained 250 mM iodoacetamide in place of the 2-mercaptoethanol or dithiothreitol (DDT). The sample was homogenized with teflon glass homogenizer and clarified by centrifugation at 13,000×g for 10 minutes. The sample was dialyzed against 0.15M NaCl, 10 mM EDTA, 1 mM N-ethylmaleimide, and 0.3 mM p-aminobenzamidine in 50 mM Tris-HCl buffer (pH 7.4). Aliquots of 15 µl were mixed with 15 µl glycerol and 3 µl 1% SDS and 0.0015% bromphenol blue containing either 5% 2-mercaptoethanol or 250 mM iodoacetamide. The samples were heated at 100° C. for 5 minutes and separated by electrophoresis on 10% polyacrylamide gel in a mini-gel apparatus (BIORAD, Protein II). The protein was electroeluted onto nitrocellulose filters and the filters were reacted with polyclonal rabbit antibodies specific for the human proα1(I) chain, specific for the human and mouse proα1(I) chain, or specific for the human proα1(II) chain. The secondary antibodies were anti-rabbit IgG coupled to alkaline phosphatase.

Cell Culturing and Labeling of Newly Synthesized Proteins

Skin fibroblasts from transgenic mice and control mice were grown at passage 5 in 25 cm$^2$ plastic flasks (Falcon Labware) in Dulbecco's modified Eagle's medium with 10% fetal calf serum. At confluency, the cells were incubated for 4 hours in 1.5 ml of fresh medium containing 50 µg/ml ascorbate and 10 µCi/ml $^{14}$C-proline (250 mCi/mmol, Amersham Corp.). At the end of the labeling period, 0.15 ml of solution containing 250 mM EDTA, 100 mM ethylmalelmide, 10 mM phenylmethanesulfonyl fluoride and 0.1% NaN$_3$ was added to each flask to prevent proteolysis. Immediately thereafter, the media was collected and the cell layer was washed three times with 2 ml of cold phosphate-buffered saline. Media was centrifuged for 5 minutes at 13,000×g at 4° C. Proteins were precipitated by two volumes of cold ethanol for 1 hour at −20° C. The precipitate was collected by centrifugation at 13,000×g for 30 minutes at 4° C., washed twice with 70% cold ethanol, and vacuum dried.

Cells were recovered from the flasks by adding 2 ml of a solution containing 50 mM ethylmalelmide, 1 mM phenylmethanesulfonyl fluoride and 0.01% NaN$_3$. The samples were incubated for 5 minutes at 4° C., frozen at −20° C., defrosted, scraped, transferred to a tube and vortexed. Insoluble material from lysate was removed by brief centrifugation. The supernatant was precipitated with two volumes of ethanol as described for media proteins.

Newly synthesized proα chains are analyzed by SDS-polyacrylamide gel electrophoresis before and after a series of protease digestions. For direct assay of the protein synthesized, the medium is removed, a cocktail of protease inhibitors added, and the protein precipitated with ammonium sulfate. The precipitated proteins are analyzed by SDS-polyacrylamide gel electrophoresis. Samples of cell layers are homogenized in buffer containing protease inhibitors and analyzed by SDS-polyacrylamide electrophoresis. For analysis of the proteins from transgenic mice containing the proα1(I) mini-gene, one-dimensional electrophoresis was carried out with SDS in a 4 to 15% gradient polyacrylamide gel. Two-dimensional electrophoresis may also be carried out with unreduced samples separated in one direction and reduced samples in a second direction. For two-dimensional analysis, the unreduced media or cellular proteins were first run in 7% polyacrylamide gel. Individual lanes were cut out from the first dimensional gel, treated with 5% 2-mercaptoethanol for 1 hour, and separated by electrophoresis in second dimension in a 12% polyacrylamide gel. Western blot analysis with polyclonal antibodies was carried out as described above. After detection of bands using antibodies, the same blots were exposed on x-ray film to detect $^{14}$C-labeled proteins and verify the identity of the proα chains. Fluorograms of exposed films are evaluated for size of polypeptide chain synthesis, post-translational overmodification, and relative amounts of polypeptide synthesized.

Proα chains and procollagen synthesized by the fibroblasts are also evaluated by SDS-polyacrylamide electrophoresis after fragmentation by pepsin, vertebrate collagenase or cyanogen bromide. In the case of exogenous genes in which new codons for cysteine have been introduced, the presence of dimers will be detected by examining fragments of proα chains with or without reduction prior to electrophoresis.

Assay of Exogenous Gene Products by Immunoprecipitation or Western Blotting

The protein on the SDS-acrylamide gels was electroeluted onto a nitrocellulose filter. The filter was then reacted with either a polyclonal antibody specific for the N-propeptide of the human proα1(I) chain or a polyclonal antibody that reacted with the C-propeptide of the proα1(I) chain from both mouse and human. The secondary antibody was anti-rabbit IgG coupled to alkaline phosphatase (Promega Biotech). To compare the relative amounts of protein synthesized from the mini-gene and the endogenous proα1(I) gene, the Western blots prepared with cross-reacting antibodies were photocopied onto transparencies and the transparencies were assayed with a densitometer. The same filter was assayed with varying intensity settings for the photocopier in order to establish that the film response was linear. The observed values for the peaks of mini-gene and endogenous gene products per mg tissue varied with the age of the mouse, apparently because of the increase in the extracellular matrix in most tissues with age. However, values for the ratio of mini-gene product to endogenous gene product was relatively constant for transgenic mice from the same line, and repeated assays of the same sample of tissue gave a standard deviation of ±25% of mean (n=5).

Example 4

Evaluation of Bones and Other Tissues in Transgenic Mice

Bone status in lines of transgenic mice is evaluated by determinations of ash weight, single photon absorptiometry, mechanical testing, staining and microradiography.

Ash weight Determination

Bones to be determined for ash weight testing are cleaned mechanically of soft tissue and a wet weight obtained and volume obtained by displacement for significant dehydration of the bone. Dry weight and ash weights are obtained as follows: The bone is placed in a crucible and dried in a muffle furnace at 100° C. until the bone weight changes by less than a percent between determination. The bone is then incinerated in the muffle oven at 580°–600° C. for 24 hours and ash weights are obtained. Ash weight can then be described both as total ash weight and ash weight per volume (the ratio of the ash weight to the initial moist volume of the bone).

Single Photon Absorptiometry

Single photon absorptiometry is performed on a standard Lunar single photon absorptiometer with a scan speed of 0.25 mm per second. Whole bone determination and single scan line determination to specific positions along the bone are obtained from evaluation of these scans. Scans are performed by immersing the bone in water in a standard plastic tray. Polycarbonate plastic stops have been glued to the tray to allow reproducible positioning of the bone samples. Manual bone edge detection is done for final bone mass determination by single photon absorptiometry.

Skeletal Morphology and Histology

To examine the skeletal morphology of transgenic mice containing the proα1(I) mini-gene, $F_1$ mice from the R-line were stained with Alizarin red and Alizarin blue in accordance with methods known in the art.

To examine the skeletal morphology and histology of transgenic mice having the proα1(II) mini-gene construct mineralized tissue of selected newborn mice was stained with Alizarin Red S. For microscopy of tissues, whole embryos were perfused with 2% paraformaldehyde and 2.5% glutaraldehyde in 0.1M phosphate buffer (pH 7.4) shortly after birth. Tissues were decalcified by incubation in 10% EDTA (pH 7.4) for 2 to 6 days. Samples were post-fixed in 1% osmium tetroxide in 0.15M cacodylate buffer (pH 7.4) for 2 to 4 hours at 20° C., washed three times with the cacodylate buffer, and then placed in 1% tannic acid in 0.15M cacodylate buffer (pH 7.4). For polarized light microscopy, specimens embedded in paraffin were stained with Dirius Red (picrosirius staining) after incubation in xylol at 37° C. overnight and with 2 mg/ml hyaluronidase (Sigma, St. Louis) in 0.1M phosphate buffer (pH 6.9) at 37° C. overnight. The sections were analyzed with an Ortholux 2 Pol-Bk microscope (Ernst Leitz GmbH, Wetzlar, FRG) operated in monochromatic light [λ=543 nm; filter IL 543 (Schott, Mainz, FRG)] and using the de Senarmont compensation technique. For electron microscopy, samples embedded in Epon were cut into 50 to 60 nm sections, stained with uranyl acetate for 30 minutes and lead citrate for 2 to 4 minutes, and examined with a JEM-1200 EX electron microscope (Jeol Ltd., Tokyo, Japan)

What is claimed is:

1. A method for controlling the synthesis of protein from the human gene for the proα1(I) chain of type I procollagen in cells, comprising:

(a) providing one or more genes selected from the group consisting of (1) a mini-gene construct of the human gene for the proα1(I) chain of type I procollagen, wherein said mini-gene construct does not contain exons 6 to 46 of the human COL1A1 gene, and (2) a mini-gene construct of the human gene for the proα1(I) chain of type I procollagen, wherein said mini-gene construct does not contain exons 6 to 46 of the human COL1A1 gene and wherein the second half of the mini-gene construct codes for an antisense sequence for exons 47 to 52 of the COL1A1 gene and the associated introns; and (b) administering by injection one or both mini-gene constructs to cells that synthesize protein from the human gene for the proα1(I) chain of type I procollagen.

2. A method for controlling collagen deposition in tissue, comprising:

(a) providing one or more genes selected from the group consisting of (1) a mini-gene construct of the human gene for the proα1(I) chain of type I procollagen, wherein said mini-gene construct does not contain exons 6 to 46 of the human COL1A1 gene, and (2) a mini-gene construct of the human gene for the proα1(I) chain of type I procollagen, wherein said mini-gene construct does not contain exons 6 to 46 of the human COL1A1 gene and wherein the second half of the mini-gene construct codes for an antisense sequence for exons 47 to 52 of the COL1A1 gene and the associated introns; and (b) administering by injection one or both mini-gene constructs to the tissue wherein the collagen deposition is to be controlled.

\* \* \* \* \*